United States Patent [19]
Wang et al.

[11] Patent Number: 5,210,313
[45] Date of Patent: May 11, 1993

[54] PREPARATION OF 2,5-DICHLOROBENZOPHENONES

[75] Inventors: Ying Wang, San Dimas; Mark S. Trimmer, Monrovia, both of Calif.

[73] Assignee: Maxdem Incorporated, San Dimas, Calif.

[21] Appl. No.: 818,629

[22] Filed: Jan. 10, 1992

[51] Int. Cl.$^5$ ............................................. C07C 45/45
[52] U.S. Cl. .................................... 568/323; 568/322; 568/319
[58] Field of Search ................ 568/323, 319, 322, 323

[56] References Cited

FOREIGN PATENT DOCUMENTS

| | | |
|---|---|---|
| 1153369 | 11/1912 | Canada . |
| 236726 | 6/1986 | Fed. Rep. of Germany ...... 568/323 |
| 2534905 | 4/1984 | France ................................. 568/323 |
| 63-115839 | 5/1988 | Japan .................................... 568/323 |
| 1118864 | 7/1968 | United Kingdom ................ 568/323 |

OTHER PUBLICATIONS

Gore, et al., "Friedel-Crafts Benzoylation of p-Dichlorobenzene", Zhurnal Organicheskoi Khimii, vol. 3, No. 6, pp. 1105-1106.
Goodman, et al., "The Mechanism for BVenzoylation of Dichlorobenzenes", Tetrahedron, vol. 32, pp. 843-845.
Goodman, et al., "The Benzoylation of o-, m- and p-Dichlorobenzenes", J. Chem. Soc. (C), 1968, pp. 2452-2454.
Pinkus, et al., "A New Organophosphorus Reaction Involving Multiple Bond-Breaking and -Making", Chemical Communications, 1967, pp. 855-856.
De Crauw, "Le Principe de la Polarite Alternante Induite en Rapport Avec Les Reactions des des Derives du Paradichlorobenzene et D'Autres Derives sur le Methylate de Sodium", Rec. Trav. Chim. Pay Bas 50, 753 (1931), pp. 752-792.
Ganzmuller, "Uber Halogenierte Benzophenone", J. Prakt. Chem 138,311 (1933), pp. 311—312.

Primary Examiner—James H. Reamer
Attorney, Agent, or Firm—Christie, Parker & Hale

[57] ABSTRACT

A method for preparing isomerically pure 2,5-dichlorobenzophenones in good to high yields is provided. The invention comprises Friedel-Crafts aroylation of 1,4-dichlorobenzene using an aroyl halide or aromatic anhydride and at least one Lewis acid, the latter being present in an amount of at least about 1.1 mole per mole of aroyl halide or aromatic anhydride, preferably about 1.5 moles per mole of aroyl halide or aromatic anhydride and, more preferably, from about 2 to about 2.5 moles of Lewis acid per mole of aroyl halide or aromatic anhydride. Preferably, the molar ratio of 1,4-dichlorobenzene to aroyl halide ranges from about 1.2:1 to about 8:1.

22 Claims, No Drawings

PREPARATION OF 2,5-DICHLOROBENZOPHENONES

FIELD OF THE INVENTION

This invention relates to methods for preparing 2,5-dichlorobenzophenones, and in particular, methods employing Friedel-Crafts aroylation of 1,4-dichlorobenzene.

BACKGROUND OF THE INVENTION

Benzophenones are very useful in organic synthesis in general and in the pharmaceutical industry in particular. Although it is common to prepare benzophenones by Friedel-Crafts benzoylation, known methods of preparing 2,5-dichlorobenzophenones from 1,4-dichlorobenzene have had very limited success and have been characterized by low conversion, low yield and difficulty in purification due to isomeric contamination of the desired 2,5-dichlorobenzophenone. Moreover, previous attempts to prepare 2,5-dichlorobenzophenones from 1,4-dichlorobenzene commonly have used nitrobenzene as a solvent. Nitrobenzene is highly toxic and its use is regulated. All of these factors limit the possibility of commercial-scale preparation of 2,5-dichlorobenzophenones from 1,4-dichlorobenzene.

In one example of the prior methods just described, after heating dichlorobenzene and benzoyl chloride with aluminum chloride for 49 hours at 150° to 170° C., 2,5-dichlorobenzophenone was obtained in only 20% yield. (Th. de Crauw, Rec. Trav. Chim. Pay Bas 50, 767, (1931)). In another case, 2,5-dichlorobenzophenone was obtained in 0.8% yield, together with appreciable amounts of other isomers, after running the reaction in nitrobenzene for 10 hours at 100° C. (P. A. Goodman et al., J. Chem. Soc. (C) 2452, (1968)). Other unsuccessful examples can be found in the literature. See, e.g., J. Ganzmuller, J. Prakt. Chem. 138, 311, (1933); p. H. Gore et al., Zh. Org. Khim., 1145, (1967) 10% yield; M. Godfrey et al., Tetrahedron, 32, 843, (1976) (0.8% yield).

Higher yields of pure 2,5-dichlorobenzophenones have been obtained by starting with 2,5-dichlorobenzoyl chloride. (B. M. Zarnegar, Canadian Patent No. 1,153,369, granted to Mobil Oil Corporation U.S.A.). This aroyl chloride is not commercially available and has to be synthesized from expensive 2,5-dichlorobenzoic acid. Moreover, when 2,5-dichlorobenzoyl chloride reacts with substituted benzenes, e.g., toluene, regiosteric isomers usually cannot be avoided. Such a synthetic scheme is unattractive.

Accordingly, a need exists for an inexpensive method for preparing isomerically pure 2,5-dichlorobenzophenone and substituted analogs from 1,4-dichlorobenzene in high yield.

SUMMARY OF THE INVENTION

It has now been discovered that 2,5-dichlorobenzophenone and a broad class of substituted analogs of 2,5-dichlorobenzophenone can be prepared in high yield and with isomeric purity using the method of Friedel-Crafts aroylation of 1,4-dichlorobenzene in the presence of a suitably large amount of Lewis acid catalyst. More specifically, heating a mixture of an aroyl halide, 1,4-dichlorobenzene and at least one Lewis acid present in an amount of at least about 1.1 mole per mole of aroyl halide, preferably about 1.5 mole per mole of aroyl halide, more preferably about 2 to about 2.5 mole of Lewis acid per mole of aroyl halide results in a high yield (greater than about 50%) of isomerically pure 2,5-dichlorobenzophenones.

A variety of substituted and unsubstituted aroyl halides can be used to produce 2,5-dichlorobenzophenone analogs in accordance with the present invention. Without limitation, these include benzenecarbonyl halides ("benzoyl halides"), arylcarbonyl halides ("aroyl halides") and heteroarylcarbonyl halides ("heteroaroyl halides"). For convenience, all of these reactants are referred to herein as "aroyl halides."

In addition to aroyl halides, other activated forms of aromatic acids can be used in the present invention, including, e.g., substituted and unsubstituted anhydrides such as phthalic anhydride, benzoic anhydride and the like.

The aroylation products of the method provided by the present invention can be used as starting materials for general, pharmaceutical and polymer synthesis.

DETAILED DESCRIPTION OF THE INVENTION

This invention provides a method of preparing pure 2,5-dichlorobenzophenone and substituted analogs in high yield from 1,4-dichlorobenzene and aroyl halides. The isomeric purity of the 2,5-dichlorobenzophenones produced is greater than about 99.5%.

The invention resides in the discovery that Friedel-Crafts aroylation of 1,4-dichlorobenzene proceeds in high yield and gives isomerically pure products if a Lewis acid catalyst is present in large amount relative to the amount of aroyl halide reactant. More particularly, the invention comprises Friedel-Crafts aroylation of 1,4-dichlorobenzene using an aroyl halide and at least one Lewis acid catalyst preferably present in an amount of at least about 1.5 mole—more preferably from about 2 to about 2.5 mole—per mole equivalent of aroyl halide.

Starting material ratios as low as 1.1/1.3/1 (moles of $AlCl_3$:1,4-dichlorobenzene:benzoyl chloride) have been found sufficient to produce 2,5-dichlorobenzophenone in about 50% yield under the conditions provided by the present invention; the same ratio of starting materials has been found to give a 64% yield of 2,5-dichlorobenzophenone if the benzoyl chloride is added slowly to a mixture of $AlCl_3$, 1,4-dichlorobenzene and a small amount of benzoyl chloride.

Higher relative amounts of Lewis acid improve yield and product purity and increase the speed of reaction. The trade-off is the cost of additional Lewis acid and increased amounts of by-products requiring disposal. Lower relative amounts of Lewis acid require a higher temperature and a longer reaction time; this may account for some of the earlier failures reported in the literature. More Lewis acid is required in the presence of donor substituents. As discussed below, excess 1,4-dichlorobenzene also has been found to improve product yields.

The products of the method described herein are 2,5-dichlorobenzophenones, meaning 2,5-dichlorobenzophenone and substituted analogs thereof. Such compounds are polynuclear aromatic ketones in which one moiety attached to the carbonyl group is a 2,5-dichlorophenyl group, and the other moiety is an aryl or heteroaryl group, which may be substituted or unsubstituted. For convenience, the term "2,5-dichlorobenzophenones" is defined to include both 2,5-dichlorobenzophenone and substituted analogs thereof.

The aroyl halides used to produce these compounds include, without limitation, substituted and unsubstituted: benzenecarbonyl halides ("benzoyl halides"), arylcarbonyl halides ("aroyl halides") and heteroarylcarbonyl halides ("heteroaroyl halides"). For purposes of nomenclature, all such compounds are referred to herein (and in the appended claims) as "aroyl halides," unless the context indicates otherwise. Structurally, the aroyl halides can be viewed as comprising benzoyl halides or heteroaroyl halides having from 0 to 5, or 0 to 4, non-hydrogen substituents bound to the benzoyl or heteroaroyl ring, respectively, each of which does not interfere with Friedel-Crafts aroylation. Each substituent is bound to the benzoyl or heteroaroyl ring either directly or through a carbon atom or a heteroatom, comprising, without limitation, sulfur, phosphorus, oxygen, nitrogen, or silicon.

For example, the aroyl halide used to prepare 2,5-dichlorobenzophenone is benzoyl chloride (or other halide: bromide, iodide, and the like), which has zero non-hydrogen substituents; the benzoyl ring has a hydrogen atom at all five positions. Similarly, an aroyl halide (actually, a heteroaroyl halide) for preparing 3'-pyridinecarbonyl-2,5-dichlorobenzene is nicotinoylhalide, which has zero non-hydrogen substituents. In contrast, 2-methoxybenzoyl chloride has one non-hydrogen substituent: a methoxy group bound to the benzoyl ring at the 2 position. 1-Naphthoyl chloride can be viewed as a benzoyl ring having two non-hydrogen substituents (both carbon atoms) bound to the benzoyl ring at adjacent ortho- and metapositions on the ring, due to the fused ring structure of naphthalene.

Any aroyl halide can be used as long as it does not interfere with aroylation. Thus, p-chloromethylbenzoyl chloride is not particularly useful because the chloromethyl group causes formation of complicated reaction products. Some non-limiting examples of useful aroyl halides are: benzoyl chloride, 1-naphthoyl chloride, 2-naphthoyl chloride, 4-quinolinoyl chloride, nicotinoyl chloride (3-pyridinecarbonyl chloride), isonicotinoyl chloride (4-pyridinecarbonyl chloride), p-toluoyl chloride, m-toluoyl chloride, o-toluoyl chloride, phthaloyl chloride, isophthaloyl chloride, terephthaloyl chloride, 4,4'-biphenyldicarbonyl chloride, 2,3-dimethylbenzoyl chloride, 2,4-dimethylbenzoyl chloride, 2,5-dimethylbenzoyl chloride, 2,6-dimethylbenzoyl chloride, 3,4-dimethylbenzoylchloride, 3,5-dimethylbenzoylchloride, 2-benzoylbenzoyl chloride, 3-benzoylbenzoyl chloride, 4-benzoylbenzoyl chloride, 2-fluorobenzoyl chloride, 3-fluorobenzoyl chloride, 4-fluorobenzoyl chloride, 2-chlorobenzoyl chloride, 3-chlorobenzoyl chloride, 4-chlorobenzoyl chloride, 2-trifluoromethylbenzoyl chloride, 3-trifluoromethylbenzoyl chloride, 4-trifluoromethylbenzoyl chloride, 2-methoxybenzoyl chloride, 3-methoxybenzoyl chloride, 4-methoxybenzoyl chloride, 2-methoxycarbonylbenzoyl chloride, 3-methoxycarbonylbenzoyl chloride, 4-methoxycarbonylbenzoyl chloride, 2-cyanobenzoyl chloride, 3-cyanobenzoyl chloride, and 4-cyanobenzoyl chloride. Aroyl halides besides aroyl chlorides may be used, including without limitation, aroyl bromides, aroyl iodides, and the like. Thus, 2,5-dichlorobenzophenone can be prepared by Friedel-Crafts aroylation of 1,4-dichlorobenzene using benzoyl bromide and at least one Lewis acid.

In addition to aroyl halides, other activated forms of aromatic acids can be reacted with 1,4-dichlorobenzene in the presence of one or more Lewis acids to produce substituted analogs of 2,5-dichlorobenzophenone. Non-limiting examples include substituted and unsubstituted aromatic anhydrides (both of which are referred to herein as aromatic anhydrides), such as phthalic anhydride, benzoic anhydride, substituted phthalic anhydrides and substituted benzoic anhydrides. The substituents (non-hydrogen atoms) on "substituted" aromatic anhydrides are limited to functional groups that do not interfere with Friedel-Crafts aroylation of 1,4-dichlorobenzene. In general, 2,5-dichlorobenzophenones prepared in accordance with the present invention can be made using an acid halide or its corresponding anhydride, including the anhydride analogs of the acid chlorides listed above. The preferred and other ratios of reactants described herein (e.g., Lewis acid-to-aroyl halide, 1,4-dichlorobenzene-to-aroyl halide) apply equally to reactions in which an aromatic anhydride is used in place of an aroyl halide.

Although not bound by theory, in view of past failures to prepare isomerically pure 2,5-dichlorobenzophenones in substantial yield using Friedel-Crafts aroylation of 1,4-dichlorobenzene in the presence of only small amounts of Lewis acids, it is believed that the present invention's success is owed to the relatively large Lewis acid-to-aroyl halide ratio used in the Friedel-Crafts aroylation of 1,4-dichlorobenzene. In particular, it is believed that side reactions are somehow suppressed, or, perhaps more correctly, the reaction of an aroyl halide or other activated aromatic acid with 1,4-dichlorobenzene is kinetically favored over side reactions when the molar ratio of Lewis acid-to-aroyl halide is large, i.e., preferably at least about 1.5:1.

As used herein, the term "isomerically pure 2,5-dichlorobenzophenones" means that, focusing on the dichlorophenyl group of the final product, and as determined by standard analytical methods, including without limitation, gas chromatography (GC), high pressure liquid chromatography (HPLC) and the like, greater than about 99.5% of the dichlorobenzophenone (or substituted analog thereof) obtained is the 2,5-dichloro isomer, as opposed to 2,3-, 2,4-, and other possible isomers. Thus, Friedel-Crafts benzoylation of 1,4-dichlorobenzene using benzoyl halide and about 1,5 mole of aluminum trichloride per mole of benzoyl halide yields 2,5-dichlorobenzophenone rather than 2,4-dichlorobenzophenone, 3,4-dichlorobenzophenone or (any) other isomer(s). Typically, no detectable isomerization of the 1,4-dichlorobenzene occurs during the reaction. In contrast, undesirable isomerization has been reported in the literature when nitrobenzene was used as a solvent. Additionally, if the 1,4-dichlorobenzene starting material is isomerically impure, isomers other than 2,5-dichlorobenzophenone can result.

It is believed that the molar ratio of dichlorobenzene to aroyl halide is also an important reaction parameter, with best results being achieved when the ratio ranges from about 1.2:1 to about 8:1 or even larger. When the ratio is less than about 1.1:1, aroylation proceeds much more slowly and the yield of dichlorobenzophenone is significantly lower. When a large excess of 1,4-dichlorobenzene is used, the excess acts as a solvent. Other solvents can be used, but 1,4-dichlorobenzene is preferred, if a solvent is used. Nitrobenzene should be avoided, because of its toxicity, expense, and the occurrence of isomerization reported to accompany its use.

Preferably, the Lewis acid catalyst is selected from the group consisting of aluminum bromide, aluminum chloride, aluminum iodide, antimony pentachloride, boron tribromide, boron trichloride, boron trifluoride, boron triiodide, ferric bromide, ferric chloride, gallium trichloride, niobium pentahalides, phosphorus trifluoride, stannic chloride, stannous halides, tantalum pentahalides, titanium tetrahalides, zinc chloride, Nafion ® (a polymeric fluorinated sulfonic acid), other solid acids such as acidic clays, metal phosphates, metal phosphonates, and the like, and mixtures thereof. Acid catalysts useful for Friedel-Crafts aroylation have been reviewed by Olah in Friedel-Crafts and Related Reactions. Part I, G. A. Olah, Ed., Wiley, N.Y., 1963. Anhydrous aluminum chloride is most preferred. Without being bound by theory, it is believed that when at least a modicum of aroyl halide is mixed with 1,4-dichlorobenzene, isomerization of the 1,4-dichlorobenzene—upon introduction of a Lewis acid—is suppressed.

The aroylation reaction is run at a temperature of from about 0° to about 250° C., preferably from about 80° to about 170° C. It is preferred to carry out the reaction under anhydrous conditions.

Pressure, the order of addition of reagents, and reaction time are not critical parameters. Most reactions are complete in three to five hours and give 2,5-dichlorobenzophenones in good yield. The end point of reaction can be monitored by thin layer chromatography and other analytical methods.

Work-up of the reaction mixture is straightforward. After the reaction is complete, it is quenched with water. Distillation of any excess 1,4-dichlorobenzene, followed by filtration and/or extraction, and recrystallization, gives an isomerically pure 2,5-dichlorobenzophenone in good to excellent yield. No isomers other than 2,5-dichlorobenzophenones have been detected, using analytical methods such as gas chromatography (GC) and high pressure liquid chromatography (HPLC).

As noted above, when the relative amount of Lewis acid is large, rather than small, the yield of reaction, product purity, and speed of reaction are all increased. However, use of a large excess of Lewis acid creates a greater quantity of by-products which must be disposed of. In particular, aluminum chloride yields HCl, Al$_2$O$_3$ and aluminum chlorohydrates, [Al$_2$(OH)$_5$Cl]$_x$ during work-up of the reaction mixture. In contrast, excess 1,4-dichlorobenzene is readily recoverable and reusable.

2,5-Dichlorobenzophenones can be used as starting materials for general, pharmaceutical and polymer synthesis. For example, the use of such compounds in the preparation of substituted para-polyphenylenes should proceed readily by metal-catalyzed aryl coupling of the 2,5-dichlorophenyl group of these compounds. Polyphenylenes formed from these compounds will have pendant side groups comprising the carbonyl and the aryl or pyridyl group bonded thereto.

EXAMPLES

The invention is further described below in several non-limiting and exemplary embodiments. All parts and percentages are by weight. Reactants are commercially available or, at a minimum, readily prepared using synthetic organic chemistry techniques known to those skilled in the art. The reactions described below can be scaled up without affecting product yield. Yields are reported as net ("isolated") yields and/or "absolute" yields, the latter being determined by gas chromatography. The difference between absolute and isolated yield reflects inefficiencies in the work-up of the reaction product.

Example 1: 2,5-Dichlorobenzophenone

To a 22 L, three-necked flask fitted with a thermometer, mechanical stirrer and a Vigreux column connected to an aqueous NaOH scrubbing tower, was added 1,4-dichlorobenzene (3 Kg, 26.4 mol) and benzoyl chloride (2.6 Kg, 18.55 mol). The mixture was heated to 80° C. to give a homogeneous solution. Aluminum chloride (5.5 Kg, 41.25 mol) was added over 12 min. with stirring. (The molar ratio of reactants was 2.2:1.4:1.0 (AlCl$_3$: Dichlorobenzene:Benzoyl Chloride)). The resulting mixture was heated to 140° C. over 60 min followed by heating to 175° C. over 30 min. Heating was stopped at 175° C. The mixture was allowed to cool to 80° C. over two hours and poured into a well stirred mixture of ice and water (ca. 25 L water and 15 Kg of ice) over 30 min. The organic solid was collected by filtration and dissolved in 7 L of toluene. The solution was washed with aqueous sodium bicarbonate and dried. Toluene was removed by distillation. Pure 2,5-dichlorobenzophenone was isolated in 80% yield after recrystallization from hexane and toluene. Gas chromatography indicated an absolute yield of 97%.

Example 2: 2,5-Dichloro-2'-methylbenzophenone

A mixture of 22 ml (0.17 mol) of 2-toluoyl chloride and 60 g (0.45 mol) of aluminum chloride in 120 g (0.82 mol) of 1,4-dichlorobenzene was heated at 170° C. with stirring in a round-bottom flask fitted with a condenser and a trap containing aqueous NaOH for collecting effluent gases. (The molar ratio of reactants was 2.6:4.8:1.0 (AlCl$_3$:Dichlorobenzene:2-Toluoyl Chloride)). After the solution was heated for 3.5 hours at this temperature, it was cooled to about 100° C., poured into ice-water and extracted with ether. The ethereal solution was distilled at atmosphere to remove ether and then distilled at reduced pressure to remove dichlorobenzene. The residue was dissolved in hexane and decolorized with charcoal. Evaporation of the solvent gave crude product. Pure 2,5-dichloro-2'-methylbenzophenone g, 59% isolated yield) was obtained after the crude product was recrystallized twice from hexane.

Example 3: 2,5-Dichloro-3,'-methylbenzophenone

The procedure of Example 2 was followed, using 22 ml (0.17 mol) of 3-toluoyl chloride and 60 g (0.45 mol) of aluminum chloride in 120 g (0.82 mol) of 1,4-dichlorobenzene. (The molar ratio of reactants was 2.6:4.8:1.0 (AlCl$_3$:Dichlorobenzene:3-Toluoyl Chloride)). Pure 2,5-dichloro-3'-methyl-benzophenone was isolated in 53% yield after the crude product was recrystallized twice from hexane.

The following qualitative examples of benzoylation of 1,4-dichlorobenzene illustrate the importance of using a large Lewis acid-to-aroyl halide ratio:

Example 4

A mixture of 40g (0.27 mol) of 1,4-dichlorobenzene, 45 g (0.34 mol) of aluminum chloride and 200 ml (1.72 mol) of benzoyl chloride was heated at 150° C. (The molar ratio of reactants was 0.20:0.16:1.00 (AlCl$_3$: Dichlorobenzene:Benzoyl Chloride)). The color of the mixture turned brownish. Evolution of hydrogen chloride gas was observed from the beginning of the reaction. After 3 hours, gas evolution virtually ceased, but heating was continued overnight to ensure completion of reaction. A very deep color was observed. Analysis by chromatography showed the formation of a small amount of 2,5-dichlorobenzophenone and large amounts of undetermined impurities.

Example 5

The reaction was carried out as in Example 4, but with 7 ml (0.06 mol) of warm 1,4-dichlorobenzene, 6 g (0.045 mol) of aluminum chloride and about 5 ml (0.043 mol) of benzoyl chloride. (The molar ratio of reactants was 1.05:1.40:1.00 (AlCl$_3$:Dichlorobenzene:Benzoyl Chloride)). After heating the mixture as in Example 4, a deep color was observed. Chromatographic analysis of the reaction mixture indicated that 2,5-dichlorobenzophenone had been produced in only low yield, along with other impurities. The conversion of benzoyl chloride appeared slow.

Example 6

A test tube was charged with 2 ml of 1,4-dichlorobenzene and a few drops of benzoyl chloride (50–100 mg). About 500 mg of aluminum chloride (5–10 equivalents per equivalent of benzoyl chloride) was added. The yellow suspension was heated with a heating gun for about 2 minutes. (The temperature was about 200° C.) Part of the mixture was hydrolysed and extracted with ether. Chromatography showed very pure 2,5-dichlorobenzophenone. Almost all of the benzoyl chloride had been consumed.

Examples 7 Through 10

In each of examples 7 through 10, the following general procedure was followed, using the amount of reactants indicated below in Table 1:

General Procedure

A mixture of 1,4-dichlorobenzene and benzoyl chloride was stirred at 80° C. Aluminum chloride was added to the mixture in one portion and the resulting mixture was stirred at 170° C. for 7 hours. The crude mixture was cooled to room temperature and hydrolysed with water. The organic material was extracted into ether and analyzed with thin layer chromatography and gas chromatography, as described below.

TABLE 1

| Example | Mass in grams (AlCl$_3$/DCB[1]/BC[2]) | Millimoles (AlCl$_3$/DCB/BC) | Molar ratio (AlCl$_3$/DCB/BC) | % Yield[3] |
|---|---|---|---|---|
| 7 | 2.1/6.17/2 | 15.8/42/14.2 | 1.1/3/1 | 73 |
| 8 | 2.1/2.7/2 | 15.8/18.4/14.2 | 1.1/1.3/1 | 50 |
| 9 | 2.42/6.17/2 | 18.2/42/14.2 | 1.1/3/1 | 85 |
| 10 | 1.8/6.17/2 | 21/41/14.2 | 1.5/3/1 | 95 |

[1]DCB is 1,4-dichlorobenzene.
[2]BC is benzoyl chloride.
[3]Yields are absolute yields of the 2,5-dichloro isomer of dichlorobenzophenone, as determined by gas chromatogrpahy, using 3-chlorobenzophenone as the internal standard. No other isomers were detected.

Example 11

A mixture of 5.4 g of 1,4-dichlorobenzene, 4.2 g of aluminum chloride and 0.5 ml of benzoyl chloride was stirred at 170° C. Additional benzoyl chloride, up to a total of 4 g, was slowly added to the mixture over 2.5 hours, and the resulting mixture was stirred for another hour at 170° C. The molar ratio of reactants was 1.1/1.3/ (AClCl$_3$:Dichlorobenzene:Benzoyl Chloride). After work-up of the crude mixture as in Examples 7 through 10, 2,5-dichlorobenzophenone was obtained in 64% yield, as determined by gas chromatography using 3-chlorobenzophenone as the internal standard.

Analytical Techniques

In each of Examples 7 through 11, gas chromatography was performed with an HP-5830A gas chromatograph with the following parameters: column: 10% SP-2100 on 80/100 SUPELCOPORT; carrier gas: helium; detector: TCD; temp.1: 140° C.; time1: 1 min.; temp.2: 350° C.; heating rate: 25° C./min.; injection temp.: 300° C.; TCD temp.: 325° C.; flow rate: 30 ml/min. The retention time of 2,5-dichlorobenzophenone was 9.5 min.

High pressure liquid chromatography was performed with a waters 600E multisolvent delivery system equipped with a waters 490E programmable multiwavelength detector, with the following parameters: column: NOVA-PAK 60A C18, 4 μm, 3.9×150 mm; mobile phase: acetonitrile/water (1:1); column head pressure: 1,236 psi; flow rate: 0.75 ml/min. The retention time of 2,5-dichlorobenzophenone was 19.02 min., which was different from those of other dichlorobenzophene isomers.

Thin layer chromatography showed that the purity of the crude (pre-work-up) 2,5-dichlorobenzophenone from examples 9 and 10 was much better than that of examples 7, 8 and 11, with example 10 being the best and example 8 the worst. Examples 8 and 11 were run with identical molar ratios for starting materials, but absolute yields of 50 and 64%, respectively, were obtained. Presumably, the difference in product yields was due to the slower rate of addition of benzoyl chloride to the reaction vessel in Example 11.

Comparison of the Present Invention with Past Procedures

Table 2 compares the reaction parameters and yields of 2,5-dichlorobenzophenone obtained in (A) the earlier synthetic efforts of other investigators, and (B) Examples 1 and 7 through 11 of the present invention.

TABLE 2

Comparison of Different Procedures of Friedel-Crafts Benzoylation of 1,4-Dichlorobenzene

| A. Prior Efforts | | | | | |
|---|---|---|---|---|---|
| Source | Molar ratio AlCl$_3$/DCB[1]/BC[2] | Solvent | Temp. (°C.) | Time | Yield (%) |
| Rec. Trav. Chim. Pay Bas 50, 767 (1931) | 0.1/0.9/1 | no | 150–170 | 49 hr. | 20 |
| J. Prakt. Chem. 138, 311, (1933) | 1.1/1.1/1 | no | small flame | 3 days | unspecified (low)[3] |
| J. Chem. Soc. Chem. Commun. 856 (1967) | unspecified | no | 150–170 | 49 hr. | 16.5 |
| Zh. Org. Khim. 1145, (1967); Tetrahedron 32, 843, (1976) | 1.2/1.2/1 | nitrobenzene | 100 | 9.5 hr. | <10 |
| J. Chem. Soc. (C) 2452, (1968) | 1/1.1/1 | nitrobenzene | 100 | 10 hr. | 0.8 |
| B. Present Invention | | | | | |
| Example | AlCl$_3$/DCB/BC | Solvent | Temp. (°C.) | Time | Yield[4] (%) |
| 1 | 2.2/1.4/1 | no | 80–175 | ≦3 hr. | 97 |

TABLE 2-continued
Comparison of Different Procedures of Friedel-Crafts Benzoylation of 1,4-Dichlorobenzene

| | | | | | |
|---|---|---|---|---|---|
| 7 | 1.1/3/1/ | no | 80–170 | ~7 hr. | 73 |
| 8 | 1.1/1.3/1 | no | 80–170 | ~7 hr. | 50 |
| 9 | 1.1/3/1 | no | 80–170 | ~7 hr. | 85 |
| 10 | 1.5/3/1 | no | 80–170 | ~7 hr. | 95 |
| 11 | 1.1/1.3/1 | no | 170 | ≧3.5 hr. | 64 |

[1]DCB is 1,4-dichlorobenzene.
[2]BC is benzoyl chloride.
[3]A numerical value is not reported in the reference itself; however, a yield of 16.5% was reported by Pinkus and Meng (J. Chem. Soc. Commun. 856 (1967)) using the experimental method described in J. Prakt. Chem., 138, 311 (1933).
[4]Yields in examples 1 and 7 through 11 are absolute yields of the 2,5-dichloro isomer of dichlorobenzophenone, as determined by gas chromatography, using 3-chlorobenzophenone as the internal standard. As isolated yield of 80% was obtained in example 1.

As shown in Table 2, prior efforts to prepare 2,5-dichlorobenzophenone by Friedel-Crafts benzoylation of 1,4-dichlorobenzene have failed, typically resulting in the production of isomerically impure 2,5-dichlorobenzophenone in only poor yield. In contrast, Friedel-Crafts aroylation of 1,4-dichlorobenzene in accordance with the present invention is an inexpensive and straightforward method for preparing isomerically pure 2,5-dichlorobenzophenone in good to excellent yield.

The invention has been described in preferred and exemplary embodiments but is not limited thereto. Those skilled in the art will appreciate that various modifications can be made without departing from the scope of the invention, which is defined by the following claims.

What is claimed is:

1. A method for preparing 2,5-dichlorobenzophenones, comprising:
   Friedel-Crafts aroylation of 1,4-dichlorobenzene using an aroyl halide or an aromatic anhydride, and at least one Lewis acid present in an amount of at least about 1.5 mole per mole of aroyl halide or aromatic anhydride.

2. A method according to claim 1, wherein said at least one Lewis acid is present in an amount of from about 2 to about 2.5 mole per mole of aroyl halide or aromatic anhydride.

3. A method according to claim 1 wherein the Lewis acid is selected from the group consisting of aluminum bromide, aluminum chloride, boron trichloride, boron trifluoride, ferric bromide, ferric chloride, stannic chloride, zinc chloride and mixtures thereof.

4. A method according to claim 1 wherein the Lewis acid is aluminum chloride.

5. A method according to claim 1, wherein the aroyl halide comprises a benzoyl halide having from 0 to 5 non-hydrogen substituents, or a heteoaroyl halide having from 0 to 4 non-hydrogen substituents, each of which said substituents does not interfere with aroylation and is bound to the aroyl halide directly or through a carbon atom or a heteroatom selected from the group consisting of sulfur, phosphorus, oxygen, nitrogen and silicon.

6. A method according to claim 1 wherein the aroyl halide is selected from the group consisting of benzoyl chloride, 1-naphthoyl chloride, 2-naphthoyl chloride, 4-quinolinoyl chloride, nicotinoyl chloride, isonicotinoyl chloride, p-toluoyl chloride, m-toluoyl chloride, o-toluoyl chloride, phthaloyl chloride, isophthaloyl chloride, terephthaloyl chloride, 4,4'-biphenyldicarbonyl chloride, 2,3-dimethylbenzoyl chloride, 2,4-dimethylbenzoyl chloride, 2,5-dimethylbenzoyl chloride, 2,6-dimethylbenzoyl chloride, 3,4-dimethylbenzoyl chloride, 3,5-dimethylbenzoyl chloride, 2-benzoylbenzoyl chloride, 3-benzoylbenzoyl chloride, 4-benzoylbenzoyl chloride, 2-fluorobenzoyl chloride, 3-fluorobenzoyl chloride, 4-fluorobenzoyl chloride, 2-chlorobenzoyl chloride, 3-chlorobenzoyl chloride, 4-chlorobenzoyl chloride, 2-trifluoromethylbenzoyl chloride, 3-trifluoromethylbenzoyl chloride, 4-trifluoromethylbenzoyl chloride, 2-methoxybenzoyl chloride, 3-methoxybenzoyl chloride, 4-methoxybenzoyl chloride, 2-methoxycarbonylbenzoyl chloride, 3-methoxycarbonylbenzoyl chloride, 4-methoxycarbonylbenzoyl chloride, 2-cyanobenzoyl chloride, 3-cyanobenzoyl chloride, and 4-cyanobenzoyl chloride.

7. A method according to claim wherein the aromatic anhydride is selected from the group consisting of phthalic anhydride, substituted phthalic anhydrides, benzoic anhydride, and substituted benzoic anhydrides.

8. A method according to claim wherein 1,4-dichlorobenzene and the aroyl halide are present in a ratio of at least about 1.2 mole of 1,4-dichlorobenzene per mole of the aroyl halide.

9. A method according to claim 8 wherein the ratio of 1,4-dichlorobenzene to aroyl halide ranges from about 1.2:1 to about 8:1.

10. A method according to claim wherein the Friedel-Crafts aroylation is carried out at a temperature of from about 0° to about 250° C.

11. A method according to claim 10 wherein the Friedel-Crafts aroylation is carried out at a temperature of from about 80° to about 170° C.

12. A method according to claim 1, wherein the 2,5-dichlorobenzophenones are isomerically pure.

13. A method for preparing 2,5-dichlorobenzophenones, comprising: Friedel-Crafts aroylation of 1,4-dichlorobenzene using an aroyl halide or an aromatic anhydride, and at least one Lewis acid, in the absence of nitrobenzene; wherein the molar ratio of Lewis acid to 1,4-dichlorobenzene to aroyl halide or aromatic anhydride is no less than about 1.1:1.3:1, and the 2,5-dichlorobenzophenones are obtained in at least about 50% yield.

14. A method according to claim 13, wherein the Lewis acid is present in an amount of from about 2 to about 2.5 mole per mole of aroyl halide or aromatic anhydride.

15. A method according to claim 12, wherein the Lewis acid is selected from the group consisting of aluminum bromide, aluminum chloride, boron trichloride, boron trifluoride, ferric bromide, ferric chloride, stannic chloride, zinc chloride and mixtures thereof.

16. A method according to claim 13, wherein the Lewis acid is aluminum chloride.

17. A method according to claim 13, wherein the aroyl halide is selected from the group consisting of benzoyl chloride, 1-naphthoyl chloride, 2-naphthoyl chloride, 4-quinolinoyl chloride, nicotinoyl chloride, isonicotinoyl chloride, p-toluoyl chloride, m-toluoyl chloride, o-toluoyl chloride, phthaloyl chloride, isophthaloyl chloride, terephthaloyl chloride, 4,4'-biphenyldicarbonyl chloride, 2,3-dimethylbenzoyl chloride, 2,4-dimethylbenzoyl chloride, 2,5-dimethylbenzoyl chloride, 2,6-dimethylbenzoyl chloride, 3,4-dimethylbenzoyl chloride, 3,5-dimethylbenzoyl chloride, 2-benzoylbenzoyl chloride, 3-benzoylbenzoyl chloride, 4-benzoylbenzoyl chloride, 2-fluorobenzoyl chloride, 3-fluorobenzoyl chloride, 4-fluorobenzoyl chloride, 2- chlorobenzoyl chloride, 3-chlorobenzoyl chloride, 4-chlorobenzoyl chloride, 2-trifluoromethylbenzoyl chloride, 3-trifluoromethylbenzoylchloride, 4-trifluoromethylbenzoyl chloride, 2-methoxybenzoyl chloride, 3-methoxybenzoyl chloride, 4-methoxybenzoyl chloride, 2-methoxycarbonylbenzoyl chloride, 3-methoxy-carbonylbenzoyl chloride, 4-methoxycarbonylbenzoyl chloride, 2-cyanobenzoyl chloride, 3-cyanobenzoyl chloride, and 4-cyanobenzoyl chloride.

18. A method according to claim 13, wherein the aromatic anhydride is selected from the group consisting of phthalic anhydride, substituted phthalic anhydrides, benzoic anhydride, and substituted benzoic anhydrides.

19. A method according to claim 13, wherein 1,4-dichlorobenzene and the aroyl halide are present in a ratio of at least about 1.2 mole of 1,4-dichlorobenzene per mole of aroyl halide.

20. A method according to claim 19, wherein the ratio of 1,4-dichlorobenzene to aroyl halide ranges from about 1.2:1 to about 8:1.

21. A method according to claim 13, wherein aroylation is carried out at a temperature of from about 0° to about 250° C.

22. A method according to claim 20, wherein aroylation is carried out at a temperature of from about 80° to about 170° C.

* * * * *

UNITED STATES PATENT AND TRADEMARK OFFICE
CERTIFICATE OF CORRECTION

PATENT NO. : 5,210,313

DATED : May 11, 1993

INVENTOR(S) : Ying Wang; Mark S. Trimmer

It is certified that error appears in the above-identified patent and that said Letters Patent is hereby corrected as shown below:

On the Title Page: item

[56] References Cited, insert the following:

-- U.S. PATENT DOCUMENTS

```
3,395,115   7/68   Milionis et al ...260/45.95
4,094,992   6/78   Kaplan et al .....424/324
4,530,844   7/85   Smerbeck et al ...514/458
4,960,945  10/90   Terauchi et al ...568/323 --
```
Title page, item [56], under References Cited,
FOREIGN PATENT DOCUMENTS, insert the following reference:

-- 1135358   12/68   United Kingdom   C07/C49/76 --

Column 6, line 43, after "methylbenzophenone" insert -- (11 --.

Column 7, line 11, after "Dichlorobenzene" insert a colon.
Column 7, line 46, below "TABLE 1" insert
  -- Starting Materials and Yields for
     Examples 7 through 10 --.
Column 7, line 53, change "1.8" to -- 2.8 --.
Column 7, line 66, change "1.1/1.3/" to -- 1.1/1.3/1 --.

UNITED STATES PATENT AND TRADEMARK OFFICE
CERTIFICATE OF CORRECTION

PATENT NO. : 5,210,313
DATED      : May 11, 1993
INVENTOR(S): Ying Wang; Mark S. Trimmer It is certified that error appears in the above-identified patent and that said Letters Patent is hereby corrected as shown below:

```
Column 10,  line 15,  after "claim" insert -- 1 --.
Column 10,  line 19,  after "claim" insert -- 1 --.
Column 10,  line 27,  after "claim" insert -- 1 --.
Column 10,  line 64,  change "3 ,4-dimethylbenzoyl" to
                      -- 3,4-dimethylbenzoyl --.
```

Signed and Sealed this

Eleventh Day of October, 1994

Attest:

BRUCE LEHMAN

*Attesting Officer*       *Commissioner of Patents and Trademarks*